United States Patent [19]

Martin

[11] Patent Number: 4,991,569

[45] Date of Patent: Feb. 12, 1991

[54] ORAL HYGIENE SHOWER NOZZLE APPARATUS

[76] Inventor: Exequiel Martin, 21281 Bristlecone, Mission Viejo, Calif. 92692

[21] Appl. No.: 274,343

[22] Filed: Nov. 21, 1988

[51] Int. Cl.$^5$ .............................................. A61H 9/00
[52] U.S. Cl. ......................................... 128/66; 4/605
[58] Field of Search .................. 128/62 A, 66; 4/605; 239/443, 447

[56] References Cited

U.S. PATENT DOCUMENTS

| | | | |
|---|---|---|---|
| 1,038,656 | 9/1912 | Reuter | 128/66 |
| 2,550,565 | 4/1951 | Hyser | 433/88 |
| 2,950,063 | 8/1960 | Ripley, Jr. | 239/443 |
| 3,500,824 | 3/1970 | Gilbert | 128/66 |
| 3,829,026 | 8/1974 | Aghnides | 239/443 |
| 3,870,045 | 3/1975 | Vaughan | 604/84 |
| 4,043,337 | 8/1977 | Bangher | 604/150 |
| 4,203,551 | 5/1980 | Levine | 239/443 |
| 4,265,229 | 5/1981 | Rice et al. | 128/66 |
| 4,303,201 | 12/1981 | Elkins et al. | 239/447 |
| 4,564,005 | 1/1986 | Marchand et al. | 128/66 |

Primary Examiner—Gene Mancene
Assistant Examiner—Adriene B. Lepiane
Attorney, Agent, or Firm—Leon Gilden

[57] ABSTRACT

An oral hygiene shower nozzle apparatus is set forth wherein a shower nozzle is provided with an apertured dispersion plate integrally and orthogonally formed to a rear portion of the nozzle with a rotating valve plate rotatably mounted parallel to and adjacent a rear face of the dispersion plate whereupon alignment of the respective apertures effects water dispersion at a forward portion of the nozzle. Rotation of the valve plate to misalign the apertures of the respective valve plate and nozzle effects water directed through a conduit to an adjoining oral hygiene tool for the cleansing of teeth by use of a conically valved dental applicator nozzle formed with an elongate flexible tube fixedly secured to the nozzle assembly rearwardly of the valve plate. Furthermore, a toothpick and dental floss holder is provided.

1 Claim, 1 Drawing Sheet

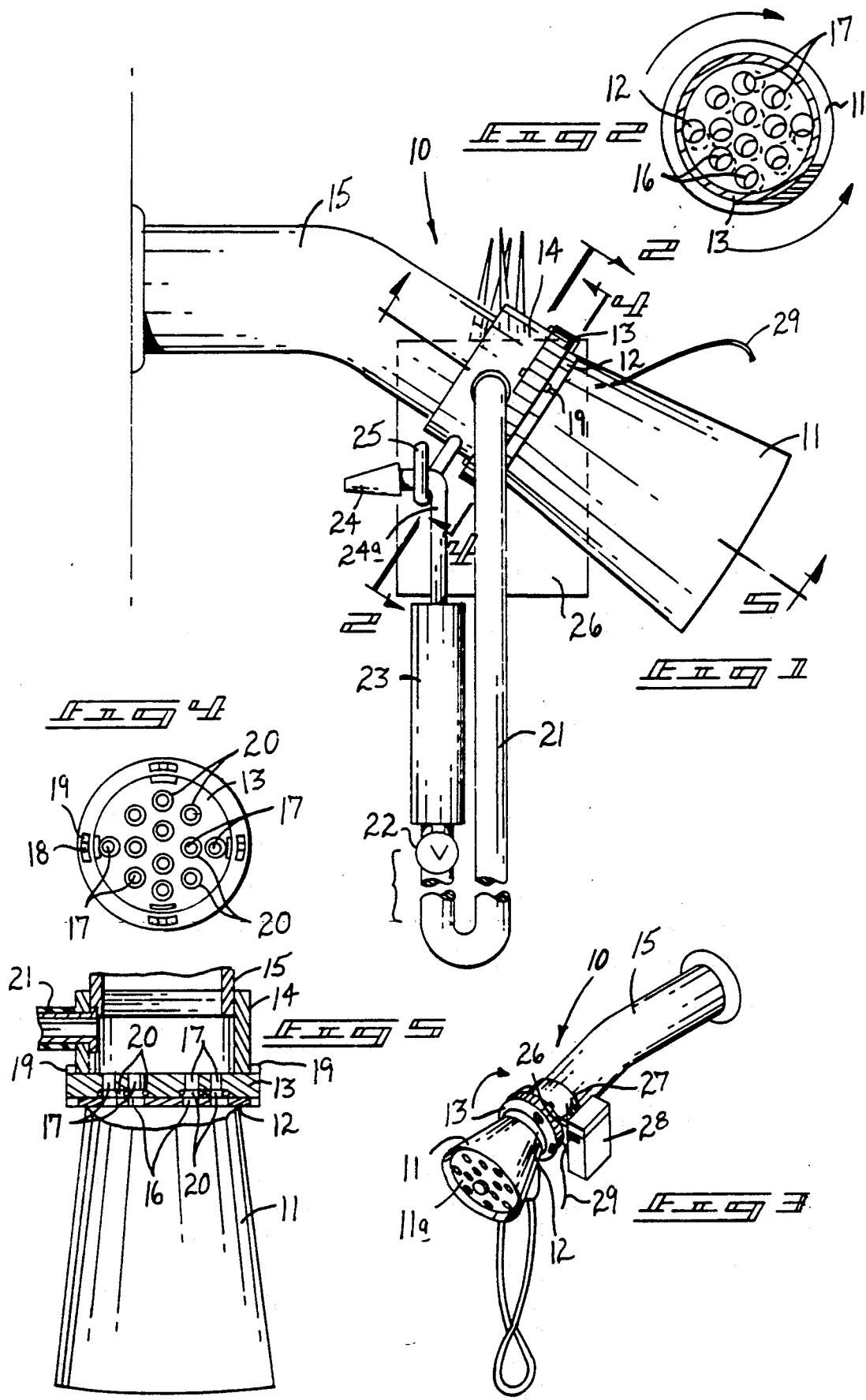

ORAL HYGIENE SHOWER NOZZLE APPARATUS

BACKGROUND OF THE INVENTION

1. Field of the Invention

The field of invention relates to shower nozzles, and more particularly pertains to a new and improved oral hygiene shower nozzle apparatus wherein the same provides selective use of a dental water applicator as well as dental floss and toothpick usage for an individual.

2. Description of the Prior Art

The use of shower nozzles in conjunction with hygienic tools is well known in the prior art. Specifically, the prior art devices have failed lo provide a complete hygienic work station that may be conveniently and readily utilized by an individual. Further, hygienic tools specifically utilizing fluid pressure are of well known in the prior art as evidenced by U.S. Pat. No. 2,550,565 to Hyser setting forth a typical water dispensing hygienic tool utilized for effective oral cleansing to avoid irritation that is typically found in brush cleaning.

U.S. Pat. No. 3,870,045 to Vaughan sets forth a hygienic tool for positioning in alignment with a water conduit adjacent a shower nozzle wherein the apparatus is provided with a diverter valve to divert water from the shower nozzle to the oral hygienic tool. The Vaughan patent does not provide the complete oral work station a set forth by the instant invention and further fails to provide a valve plate structure as set forth by the instant application for effective water diversion from a shower nozzle to a hygienic tool.

U.S. Pat. No. 4,043,337 to Baugher sets forth a dental syringe provided with a valve operatively secured to a shower nozzle, but as in the prior application fails to provide a complete oral cleansing work station and additionally, the valve utilized by the Baugher patent does not provide for a multi-apertured valve plate for shower head water dispersion modification as set forth by the instant invention.

U S. Pat. No. 4,265,229 to Rice sets forth an oral hygiene apparatus for attachment to a water conduit associated with a shower nozzle wherein screw-type valve is utilized within the conduit to divert water from a shower head to the hygienic tool, as opposed to the multi-apertured plate valve as set forth by the instant invention.

U.S. Pat. No. 4,564,005 to Marchand sets forth an oral hygienic tool associated with a conduit adjacent a shower nozzle wherein a slide-type valve is utilized in conjunction with the hygienic tool to divert water from the nozzle to the tool.

As may be appreciated therefore, there continues to be a need for a new and improved oral hygiene shower nozzle apparatus which addresses both the problems of providing a complete oral hygiene work station in conjunction with a shower nozzle and providing a diverter valve to selectively divert water to the shower nozzle and water hygiene tool and in this respect, the present invention substantially fulfills this need.

SUMMARY OF THE INVENTION

In view of the foregoing disadvantages inherent in the known types of shower nozzles in association with oral hygiene tools now present in the prior art, the present invention provides an oral hygiene shower nozzle apparatus wherein the same provides a multi-faceted oral hygiene work station for enabling complete oral hygiene operation. As such, the general purpose of the present invention, which will be described subsequently in greater detail, is to provide a new and improved oral hygiene shower nozzle apparatus which has all the advantages of the prior art oral hygiene tools and none of the disadvantages.

To attain this, the present invention comprises a shower nozzle formed with a plurality of apertures in a fixed dispersion plate formed with an adjacent rotatable valve plate formed with a complementary series of apertures that are aligned or misaligned to selective degrees to enable fine adjustment of water pressure applied selectively to the shower nozzle and an associated oral hygiene fluid tool, and further providing a dental floss and toothpick dispenser fixedly secured adjacent the valve plate to enable the complete oral hygiene station available to a user.

My invention resides not in any on of these features per se, but rather in the particular combination of all of them herein disclosed and claimed and it is distinguished from the prior art in this particular combination of all of its structures for the functions specified.

There has thus been outlined, rather broadly, the more important features of the invention in order that the detailed description thereof that follows may be better understood, and in order that the present contribution to the art may be better appreciated. There are of course additional features of the invention that will be described hereinafter and which will form the subject matter of the claims appended hereto. Those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

Further, the purpose of the foregoing abstract is to enable the U.S. Patent and Trademark Office and the public generally, and especially the scientists, engineers and practitioners in the art who are not familiar with patent or legal terms or phraseology, to determine quickly from a cursory inspection the nature and essence of the technical disclosure of the application. The abstract is neither intended to define the invention of the application, which is measured by the claims, nor is it intended to be limiting as to the scope of the invention in any way.

It is therefore an object of the present invention to provide a new and improved oral hygiene shower nozzle apparatus which has all the advantages of the prior art oral hygiene shower nozzle apparatus and none of the disadvantages.

It is another object of the present invention to provide a new and improved oral hygiene shower nozzle apparatus which may be easily and efficiently manufactured and marketed.

It is a further object of the present invention to provide a new and improved oral hygiene shower nozzle apparatus which is of a durable and reliable construction.

An even further object of the present invention is to provide a new and improved oral hygiene shower nozzle apparatus which is susceptible of a low cost of manufacture with regard to both materials and labor, and which accordingly is then susceptible of low prices of sale to the consuming public, thereby making such oral hygiene shower nozzle apparatus economically available to the buying public.

Still yet another object of the present invention is to provide a new and improved oral hygiene shower nozzle apparatus which provides in the apparatuses and methods of the prior art some of the advantages thereof, while simultaneously overcoming some of the disadvantages normally associated therewith.

Still another object of the present invention is to provide a new and improved oral hygiene shower nozzle apparatus wherein the same provides for a multi-station oral hygiene apparatus and further provides for an improved valve assembly to selectively adjust hydraulic pressure to a shower nozzle and associated fluid oral hygiene tool.

These together with other objects of the invention, along with the various features of novelty which characterize the invention, are pointed out with particularity in the claims annexed to and forming a part of this disclosure. For a better understanding of the invention, its operating advantages and the specific objects attained by its uses, reference should be had to the accompanying drawings and descriptive matter in which there is illustrated preferred embodiments of the invention.

BRIEF DESCRIPTION OF THE DRAWINGS

The invention will be better understood and objects other than those set forth above will become apparent when consideration is given to the following detailed description thereof. Such description makes reference to the annexed drawings wherein:

FIG. 1 is an orthographic side view taken in elevation of the instant invention.

FIG. 2 is an orthographic view taken along the lines 2—2 of FIG. 1 in the direction indicated by the arrows.

FIG. 3 is an isometric illustration of the instant invention.

FIG. 4 is an orthographic view taken along the lines 4—4 of FIG. 1 in the direction indicated by the arrows FIG. 5 is an orthographic view taken along the lines 5—5 of FIG. 1 in the direction indicated by the arrows.

DESCRIPTION OF THE PREFERRED EMBODIMENT

With reference now to the drawings, and in particular to FIGS. 1 to 5 thereof, a new and improved oral hygiene shower nozzle apparatus embodying the principles and concepts of the present invention and generally designated by the reference numeral 10 will be described.

More specifically, it will be noted that the oral hygiene shower nozzle apparatus 10 essentially comprises an outwardly flared shower head 11 formed with a forwardly oriented discharge plate 11a and an integral rearwardly positioned dispersion plate 12. Adjacent the dispersion plate 12 is a rotatable valve plate 13 rotatable relative to the dispersion plate 12 and the conduit boss 14 threadedly or mechanically secured to the water conduit 15.

The dispersion plate 12 formed to the shower head 11 is formed with a matrix of first apertures 16. The rotatable valve plate 13 is formed with a matrix of second apertures 17 that are coextensive with the first apertures 16 in a first position and rotatable and displaced relative to the first aperture 16 in a second position to prevent transfer of water through the valve plate 13 to the shower head 11 by way of the first aperture 16 formed through the dispersion plate 12.

A plurality of bridge members 18 integrally secure the conduit boss and the shower head 11 together to enable rotation of the valve plate 13 relative thereto wherein the bridge members 18 are positioned through arcuate slots 19 formed through a perimeter of the valve plate 13 to enable rotation of the valve plate 13 relative to the conduit boss 14 and shower head 11.

Each of the second apertures 17 formed in the valve plate 18 have formed therearound an "0" ring 20 of a thickness approximately equal to the spacing between the dispersion plate 12 and the valve plate 13 to ensure a sealing relationship between each associated aperture 16 and 17 respectively. The apertures 16 and 17, as noted above, are formed in an equal matrix arrangement to enable alignment of the apertures in the first position and masking of the apertures 16 when the second apertures and associated valve plate 13 are rotated to a second position. FIG. 2 illustrates the relative rotation of the valve plate 13 to the dispersion plate 12 where only a partial masking of the first apertures are illustrated to enable a user to utilize the shower as well as the oral hygiene tool of the instant invention.

The oral hygiene tool comprises a flexible hose 21 secured through the conduit boss 14 in fluid communication with the water conduit 15. A conduit valve 22 enables a user to shut off fluid flow through the associated outlet nozzle 24 of the tool. Enlarged rigid handle 23 enables enhanced grasping of the tool and is connected by rigid conduit 24a to the outlet nozzle 24. When not in use, the rigid conduit 24a is secured upon a hook 25 integrally secured to the conduit boss 15.

Diametrically opposed to the positioning of the flexible hose 21 and its association to the conduit boss 14, is a toothpick case 26 for securement of a plurality of toothpicks 27 wherein the toothpick case 26 is sandwiched between the conduit boss 14 and a dental floss container 28 containing a spool of dental floss 29 therein for dispensing as required by a user.

The instant invention, by means of the rotatable valve plate 13, enables a partial and enhanced adjustment of fluid flow through the dispersion plate 12 and ultimately the shower head 11 to enable a user enjoyment of the shower head 11 and simultaneous utilization of the hygiene tool wherein sufficient water pressure is available throughout with nozzle 24 to enable simultaneous showering and utilization of the nozzle 24 to provide for a cleaning of a user's gums and teeth.

The manner of usage and operation of the instant invention therefore should be apparent from the above description and therefore no further discussion relative to the manner of usage and operation of the instant invention shall be provided.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

What is claimed as being new and desired to be protected by Letters Patent of the United States is as follows:

1. An oral hygiene shower nozzle apparatus for fluid engagement with a water conduit comprising, in combination, a shower head formed with a forward water discharge plate formed with water openings therethrough and a rear dispersion plate formed with a matrix of first apertures, and a valve means for selectively directing water flow to said first apertures and rotatably mounted between and adjacent said dispersion plate and a conduit boss, said conduit boss mounted for securement to said water conduit with an oral hygiene tool operatively secured in fluid communication through said conduit boss, and a conduit valve positioned in said oral hygiene tool, and wherein said valve means comprises a plate member formed with a matrix of second apertures, ad said second apertures are aligned with said first apertures when said valve means is rotated in a first position, and said second apertures are displaced with and misaligned from said first apertures when said valve means is rotated in a second position to restrict water communication from said second apertures to said first apertures, and wherein each of said second apertures has formed therearound an "O" ring means for sealing communication of said first apertures to said second apertures wherein said "O" ring means are of a thickness at least equal to a spacing defined between said valve means and said dispersion plate, and wherein said oral hygiene tool includes a flexible conduit secured in water communication with said conduit boss at one end and secured to an enlarged grip member at its other end with said conduit valve positioned adjacent said grip member, and wherein said conduit boss includes an outwardly projecting hook for selective securement of said oral hygiene tool thereto, and wherein said conduit boss includes a toothpick case integrally secured to said conduit boss and a dental floss case integrally secured to said toothpick case wherein said toothpick case and said dental floss case are integrally secured to the conduit boss diametrically opposed to said oral hygiene tool, and wherein a plurality of bridge members extend through arcuate slots formed in said valve means to integrally secure said conduit boss and said shower head together and enable rotation of said valve means relative to said conduit boss and shower head.

* * * * *